United States Patent
Larsen et al.

(10) Patent No.: US 11,396,510 B2
(45) Date of Patent: Jul. 26, 2022

(54) GABAA RECEPTOR LIGAND

(71) Applicant: Saniona A/S, Glostrup (DK)

(72) Inventors: Janus S. Larsen, Glostrup (DK); Dipak Amrutkar, Glostrup (DK); Thomas Amos Jacobsen, Glostrup (DK); Tino Dyhring, Glostrup (DK); Karin Sandager Nielsen, Glostrup (DK)

(73) Assignee: Saniona A/S, Glostrup (DK)

( * ) Notice: Subject to any disclaimer, the term of this patent is extended or adjusted under 35 U.S.C. 154(b) by 0 days.

(21) Appl. No.: 17/272,971

(22) PCT Filed: Sep. 13, 2019

(86) PCT No.: PCT/EP2019/074465
§ 371 (c)(1),
(2) Date: Mar. 3, 2021

(87) PCT Pub. No.: WO2020/053377
PCT Pub. Date: Mar. 19, 2020

(65) Prior Publication Data
US 2021/0332042 A1 Oct. 28, 2021

(30) Foreign Application Priority Data
Sep. 13, 2018 (EP) .................................. 18194297

(51) Int. Cl.
*C07D 471/04* (2006.01)
*A61P 17/06* (2006.01)
*A61P 25/02* (2006.01)
*A61P 17/04* (2006.01)

(52) U.S. Cl.
CPC ............ *C07D 471/04* (2013.01); *A61P 17/04* (2018.01); *A61P 17/06* (2018.01); *A61P 25/02* (2018.01)

(58) Field of Classification Search
CPC ........ C07D 471/04; A61P 17/06; A61P 17/04; A61P 25/02
See application file for complete search history.

(56) References Cited

U.S. PATENT DOCUMENTS 10,786,513 B2 * 9/2020 Zeilhofer ............... A61K 31/53

FOREIGN PATENT DOCUMENTS

| EP | 0616807 A1 | 9/1994 |
|---|---|---|
| WO | 98/34923 A1 | 8/1998 |
| WO | 99/67245 A1 | 12/1999 |
| WO | 2000/044752 A1 | 8/2000 |
| WO | 01/18000 A1 | 3/2001 |
| WO | 03/86406 A1 | 10/2003 |
| WO | 03/87099 A1 | 10/2003 |
| WO | 03/99816 A1 | 12/2003 |
| WO | 2004/087690 A2 | 10/2004 |
| WO | 2007/110374 A1 | 10/2007 |
| WO | 2010/055132 A1 | 5/2010 |
| WO | 2017/129801 A1 | 8/2017 |

OTHER PUBLICATIONS

Knabl et al., "Genuine antihyperalgesia by systemic diazepam revealed by experiments in GABAA receptor point-mutated mice", Pain, 2009, 141, 233-238.
McKernan et al., "Which GABAA-receptor subtypes really occur in the brain?", 1996, Trends in Neuroscience 19, 139-143.
Munro et al., "Comparison of the Novel Subtype-Selective GABAA Receptor Positive Allosteric Modulator NS11394 [3-[5-(1-Hydroxy-1-methyl-ethyl)-benzoimidazol-1-yl]-biphenyl-2-carbonitrile] with Diazepam, Zolpidem, Bretazenil, and Gaboxadol in Rat Models of Inflammatory and Neuropathic Pain", JPET, 2008, 327, 969-981.
Munro et al., "GABAA receptor modulation: Potential to deliver novel pain medicines?", European Journal of Pharmacology, 2013, 716, 1-3, 17-23.
Ross et al., "Loss of inhibitory interneurons in the dorsal spinal cord and elevated itch in Bhlhb5 mutant mice", Neuron, 2010, 65, 886-98.
Zeilhofer et al., "GABAergic analgesia: new insights from mutant mice and subtype selective agonists", Trends in Pharmacological Science, 2009, 397-402.

* cited by examiner

*Primary Examiner* — Timothy R Rozof
(74) *Attorney, Agent, or Firm* — BakerHostetler

(57) ABSTRACT

The present invention relates to 2-(3-(3-(2,4-dimethoxypyrimidin-5-yl)phenyl)-3H-imidazo[4,5-b]pyridin-6-yl)propan-2-ol, which is useful as a GABA receptor modulator. In one embodiment, said compound is useful in the treatment of pain, neuropathic pain and/or itch.

11 Claims, 5 Drawing Sheets

A

B

GABAA RECEPTOR LIGAND

CROSS-REFERENCE TO RELATED APPLICATIONS

This application is the National Stage of International Patent Application No. PCT/EP2019/074465 filed Sep. 13, 2019, which claims the benefit of European Patent Application No. 18194297.0 filed Sep. 13, 2018, the disclosure of which is incorporated herein by reference in its entirety for any and all purposes.

TECHNICAL FIELD

The present invention relates to 2-(3-(3-(2,4-dimethoxy-pyrimidin-5-yl)phenyl)-3H-imidazo[4,5-b]pyridin-6-yl)propan-2-ol, which is useful as a GABA receptor modulator. In one embodiment, said compound is useful in the treatment of pain, neuropathic pain and/or itch.

BACKGROUND

GABA is the main inhibitory neurotransmitter in the CNS including lamina-II of the spinal cord dorsal horn, where nociceptive fibres terminate. The inhibitory neurotransmission in the spinal cord is of great importance in pain transmission and enhancement of inhibition leads to analgesia (Zeilhofer HU. et. al. (2009), Trends in pharmacological science).

Modulators of $GABA_A$ receptors have been found to mediate profound analgesia in animal models of neuropathic pain (Munro, G. et al. (2013) European Journal of Pharmacology, 716, 1-3, 17-23). Current therapies for the management of neuropathic pain are of limited benefit to many patients, and involve undesirable side effects or dose-limiting toxicities. In addition, current therapies are symptomatic, not disease modifying. Needs remain for improved therapies for the management and treatment of neuropathic pain, especially those that have the capacity to modify the disease.

In addition, it has previously been demonstrated that $GABA_A$ receptor ligands may be useful in the treatment of itch (see e.g. WO 2017/129801).

The $GABA_A$ receptors are ligand gated channels which exists in multiple isoforms. Each receptor is a pentameric complex comprising subunits drawn from $\alpha_{1-6}$, $\beta_{1-3}$, $\gamma_{1-3}$, $\delta$, $\epsilon$ and $\theta$ subunit isoforms. The majority of $GABA_A$ receptors present in the CNS contain two $\alpha$, two $\beta$, and one $\gamma$ subunit (Mckernan R M. et. al. (1996). Trends in Neuroscience 19, 139-43). The pharmacological effects of activating a $GABA_A$ receptor depend mainly on which type of subunits the receptor contains. The classical anxiolytic benzodiazepines show no subtype selectivity. It has been suggested that one of the key elements in the disadvantages of the classical benzodiazepines (such as sedation, dependency, and cognitive impairment) relates to the $\alpha_1$ subunit of the $GABA_A$ receptor. Recent studies using mice with point mutations rendering the different $\alpha$ subunits insensitive to diazepam, suggest that $\alpha_2$ and $\alpha_3$ subunits mediate the analgesic effects of benzodiazepines (Knabl J. et al. (2009). Pain 141, 233-38). This is supported by pharmacological studies showing analgesic effects of selective positive modulators of $\alpha_{2/3}$ containing $GABA_A$ receptors in preclinical pain models (Munro G. et. al (2008). JPET, 327, 969-81). Thus, compounds with selectivity for the $\alpha_2$ and/or $\alpha_3$ subunits over the $\alpha 1$ subunit are expected to have an improved side effect profile.

Further, lack of GABAergic interneuron mediated inhibition in the spinal cord has been shown to be responsible for chronic itch in Bhlhb5 mutant mice (Ross S E. et. al. (2010). Neuron 65, 886-98) suggesting potential therapeutic activity by enhancement of spinal inhibition.

WO 98/34923, EP 0616807, WO 2004/087690, WO 2007/110374 and WO 2010/055132 describe benzimidazole derivatives useful in the treatment of central nervous system diseases and disorders, which are responsive to modulation of $GABA_A$ receptor complex.

WO 03/086406, WO 03/087099, WO 03/099816 and WO 01/18000 disclose imidazo-pyridine derivatives useful as ligands for GABA receptors.

WO 2000/044752 and WO 99/67245 disclose triazolo-pyridazine derivatives useful as ligands for GABA receptors.

These previously presented GABA receptor modulators indicate that minor structural differences may have a large impact on the biological activity.

However, many of the previously presented modulators of GABA receptors are associated with unwanted side effects. Thus, there is a strong need for compounds with an optimized pharmacological profile and without the unwanted side effects.

SUMMARY

In a major aspect, the present invention concerns 2-(3-(3-(2,4-dimethoxypyrimidin-5-yl)phenyl)-3H-imidazo[4,5-b]pyridin-6-yl)propan-2-ol, depicted in formula 1 (compound 1).

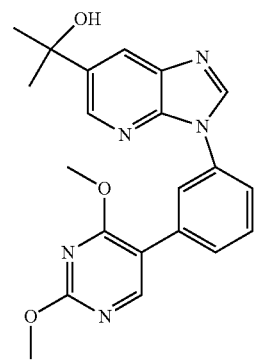

Furthermore, the present invention relates to the use of compound 1 as a medicament. The present inventors have found that compound 1 is a novel $GABA_A$ $\alpha_3$ receptor preferring positive allosteric modulator. Thus, in one aspect, compound 1 is used in the treatment, prevention, and/or alleviation of neuropathic pain. In another aspect, compound 1 is used in the treatment, prevention, and/or alleviation of itch.

DETAILED DESCRIPTION

Figure 1:
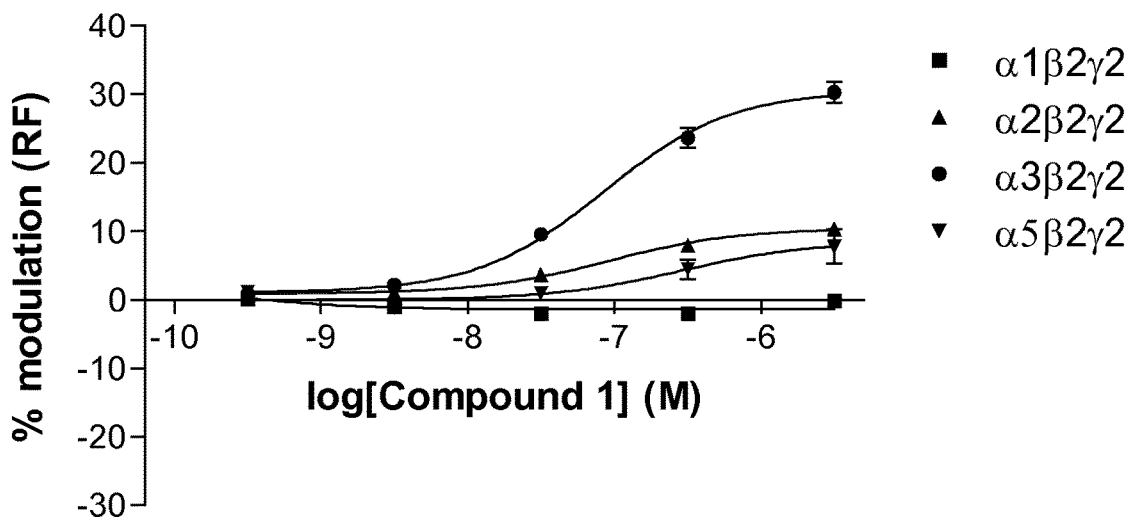
FIG. 1. (A) Compound 1, (B) Compound 9. Efficacy profile on $GABA_A$ receptors in oocyte two-electrode voltage clamp recordings. For each experimental data set, GABA was dissolved in an oocyte ringer solution in a concentration (0.5-3 μM) giving rise to $EC_{10-20}$ elicited currents for a given $GABA_A$ receptor subtype combination. Peak currents were read and normalized to a maximal effective concentration of diazepam, where after data points were fitted to the empirical Hill equation by non-linear regression, n=3-14. Compound 1 display a preferential potentiation of GABA-mediated currents in $GABA_A$-$\alpha_3$ containing receptors, a minor activation (less than 10%) of $GABA_A$-$\alpha_{2/5}$ subunits and no activation of $GABA_A$-$\alpha_1$ containing receptors.
Figure 1:
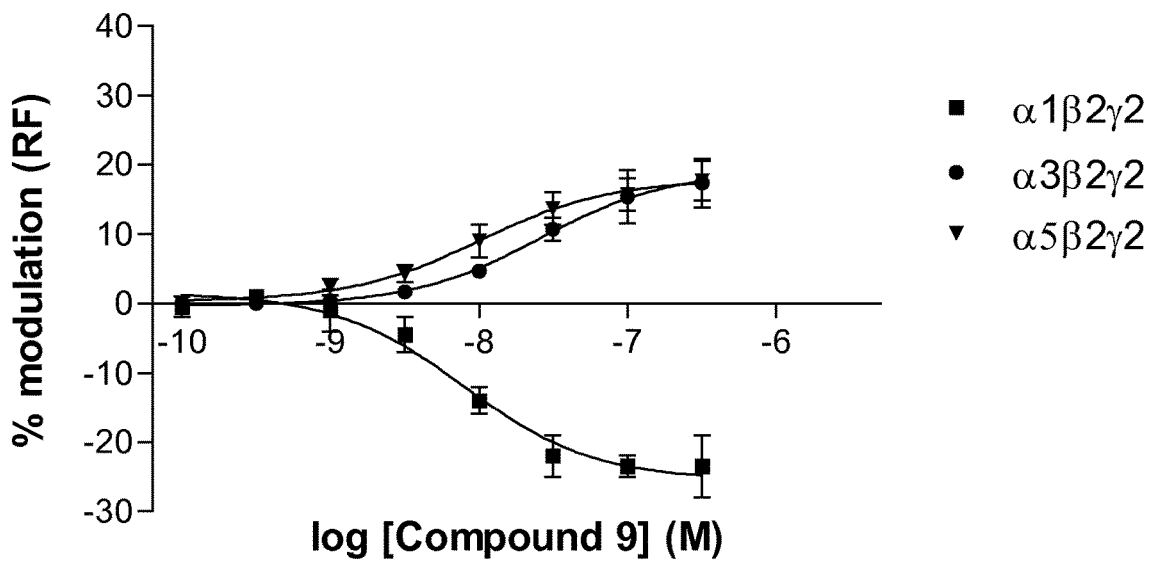

In one aspect, the present invention concerns 2-(3-(3-(2, 4-dimethoxypyrimidin-5-yl)phenyl)-3H-imidazo[4,5-b]pyridin-6-yl)propan-2-ol, depicted in formula 1.

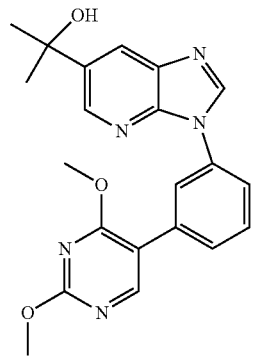

In one embodiment, compound 1 is a pharmaceutically acceptable salt.

The compound of the invention may exist in a tautomeric form.

Pharmaceutically Acceptable Salts

The chemical compound of the invention may be provided in any form suitable for the intended administration, including pharmaceutically (i.e. physiologically) acceptable salts. Examples of pharmaceutically acceptable addition salts include, without limitation, non-toxic inorganic and organic acid addition salts such as hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate, toluene-p-sulphonate, and the like. Such salts may be formed by procedures well known and described in the art. Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of compound 1 of the invention include, without limitation, the sodium, the potassium, the calcium, the magnesium, the zinc, the aluminium, the lithium, the choline, the lysinium, and the ammonium salt, and the like, of compound 1 of the invention containing an anionic group. Such cationic salts may be formed by procedures well known and described in the art. In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Labelled Compounds

The chemical compound of the present invention may be used in its labelled or un-labelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging. The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallization, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The invention also provides pharmaceutical compositions comprising therapeutically effective amount of compound 1, or a pharmaceutically acceptable salt thereof, together with at least one pharmaceutically acceptable carrier, excipient or diluent.

While compound 1 of the present invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof. Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

Compound 1 of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Compound 1 of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from compound 1 of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

A therapeutically effective dose refers to that amount of active ingredient, which ameliorates the symptoms or condition. Therapeutic efficacy and toxicity, e.g. $ED_{50}$, may be determined by standard pharmacological procedures in cell cultures or experimental animals. The dose ratio between therapeutic and toxic effects is the therapeutic index and may be expressed by ratio between plasma levels resulting in therapeutic effects and plasma ratios resulting in toxic effects. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 10.000 mg of active ingredient per individual dose, preferably of from about 1 to about 1000 mg, most preferred of from about 10 to about 500 mg, are suitable for therapeutic treatments. The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Biological Activity

Compound 1 of the present invention is capable of modulation the $GABA_A$ receptor complex, and is demonstrated to be a positive allosteric modulator (PAM) of $GABA_A$ receptors containing the $a_3$ subunit and to a minor extend, $a_2$ and $a_5$ subunits. Compound 1 reverses mechanical allodynia in a rat model for neuropathic pain after actue- and chronic treatment and it ameliorates scratching in mice treated with an itch-inducing compound suggesting analgesic as well as antipruritic effects. Compound 1 does not show liability for sedative and motor impairing effects as measured in rat exploratory locomotor activity and rotarod performance.

Methods of Therapy

Being a ligand for $GABA_A$ receptors, compound 1 is of use in the treatment, prevention, and/or alleviation of disorders of a living body, including human. Preferably, compound 1 is use in the treatment, prevention, and/or alleviation of pain, such as neuropathic pain, and/or itch.

Treatment of Neuropathic Pain

In one aspect, the present invention concerns the use of 2-(3-(3-(2,4-dimethoxypyrimidin-5-yl)phenyl)-3H-imidazo[4,5-b]pyridin-6-yl)propan-2-ol, depicted in formula 1 in the treatment, prevention, and/or alleviation of neuropathic pain.

Neuropathic pain is a category of pain that includes several forms of chronic pain and which results from dysfunction of nervous rather than somatic tissue. Neuropathic pain, that is pain deriving from dysfunction of the central or peripheral nervous system, may also be a consequence of damage to peripheral nerves or to regions of the central nervous system, may result from disease, or may be idiopathic. Symptoms of neuropathic pain include sensations of burning, tingling, electricity, pins and needles, paresthesia, dysesthesia, stiffness, numbness in the extremities, feelings of bodily distortion, allodynia (pain evoked by stimulation that is normally innocuous), hyperalgesia (abnormal sensitivity to pain), hyperpathia (an exaggerated pain response persisting long after the pain stimuli cease), phantom pain, and spontaneous pain.

Treatment of Itch

In one aspect, the present invention concerns the use of 2-(3-(3-(2,4-dimethoxypyrimidin-5-yl)phenyl)-3H-imidazo[4,5-b]pyridin-6-yl)propan-2-ol, depicted in formula 1, in the treatment, prevention, and/or alleviation of itch.

Itch (also known as Pruritus) is a sensation that causes the desire or reflex to scratch. It has been shown that itch has many similarities to pain. Most cases of itching are histamine related, and is treated with treated with antihistamines. However, some cases of itching are not treatable with antihistamines. Possible causes of itch include dry skin, skin conditions and rashes, internal diseases, nerve disorders, irritation and allergic reactions, drugs and pregnancy.

Many skin disorders, such as skin conditions, dandruff, punctate palmoplantar keratoderma, scabies, scar growth, xerosis, lice, chickenpox and hives, cause itch. Said skin conditions include psoriasis, eczema (dermatitis), sunburn, athlete's foot, and hidradenitis suppurativa.

Itchy skin can be a symptom of an underlying illness. These include liver disease, kidney failure, diabetes mellitus, hyperparathyroidism, iron deficiency anemia, jaundice, cholestasis, uraemia, polycythemia, thyroid problems and cancers, including leukemia and lymphoma. Conditions that affect the nervous system—such as multiple sclerosis, diabetes mellitus, pinched nerves and shingles (herpes zoster)—can cause itching.

Itching can be provoked or enhanced by a number of materials and chemical substances such as wool, cosmetics, soaps, histamine, opioids, prostaglandins, proteases, cytokines, neuropeptides, in particular substance P, serotonin, chloroquine Compound48/80 (CAS NO. 94724-12-6) and bile salts. Food allergies may also cause skin to itch.

Factors that are believed to enhance the sensation of itching include dryness of the epidermis and dermis, anoxia of tissues, dilation of the capillaries, irritating stimuli, primary skin diseases and psychiatric disorders.

In one embodiment, the itch is Pruritus. In one embodiment, the Pruritus is Pruritus ani. In one embodiment, the Pruritus is Pruritus scroti. In one embodiment, the Pruritus is Pruritus vulvae. In one embodiment, the Pruritus is Anogenital pruritus.

EXAMPLES

Example 1: Preparation of 2-(3-(3-(2,4-dimethoxypyrimidin-5-yl)phenyl)-3H-imidazo[4,5-b]pyridin-6-yl)propan-2-ol (1)

Step 1: Preparation of methyl 6-((3-bromophenyl)amino)-5-nitronicotinate (4)

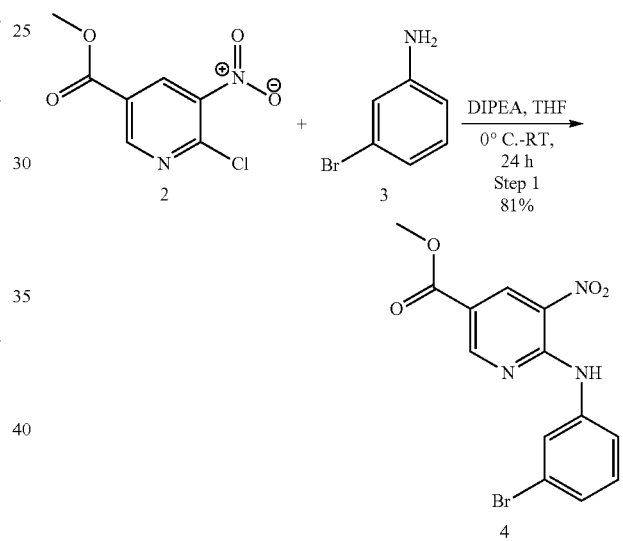

To a stirred solution of 6-chloro-5-nitro-nicotinic acid 2 (100 g, 461.72 mmol) in anhydrous tetrahydrofuran (750 mL) at 0° C. was added N,N-disopropylethylamine (120.6 mL, 692.58 mmol) followed by 3-Bromoaniline 3 (55 ml, 494.1 mmol) dropwise. The reaction mixture was stirred at ambient temperature for 24 h under nitrogen atmosphere. The reaction was monitored by TLC and UPLC. The reaction mixture was concentrated to half of its initial volume under reduced pressure. Pet ether (800 mL) was added to the reaction mixture and the suspension was stirred for 1 h. The appeared orange solid was filtered under suction and washed thoroughly with pet ether (8×300 mL) to furnish methyl 6-((3-bromophenyl)amino)-5-nitronicotinate 4 (132 g, 81%) as orange solid.

$^1$H NMR (400 MHz, DMSO-$d_6$): δ=10.31 (s, 1H, exchangeable proton), 8.94 (s, 1H), 8.82 (s, 1H), 7.92 (s, 1H), 7.63 (d, J=7.60 Hz, 1H), 7.41-7.36 (m, 2H), 3.88 (s, 3H); LCMS (ESI): m/z: 352.9 (M+FH)$^+$.

Step 2: Preparation of methyl 5-amino-6-((3-bromophenyl)amino)nicotinate (5)

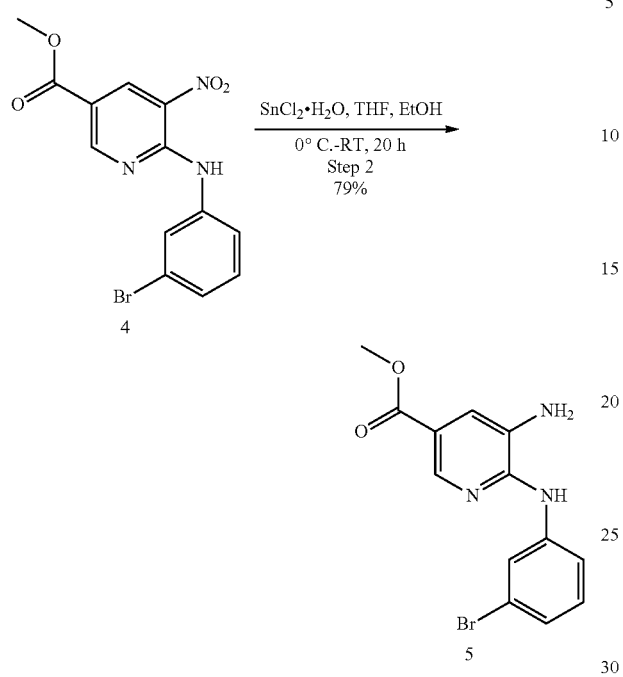

Step 3: Preparation of methyl 3-(3-bromophenyl)-3H-imidazo[4,5-b]pyridine-6-carboxylate (6

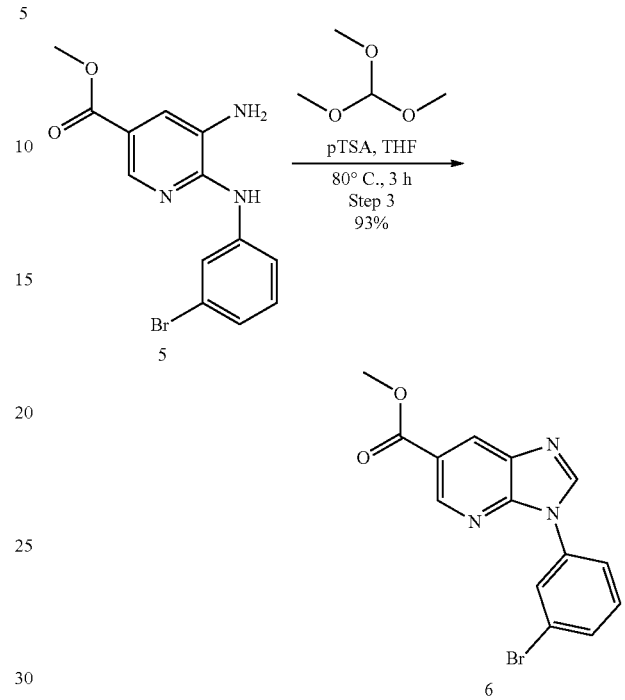

To a cooled (0° C.) suspension of methyl 6-((3-bromophenyl)amino)-5-nitronicotinate 4 (485 g; 1377.28 mmol) in a mixture of Ethanol: THF [1:1; (2600 mL)], was added stannous chloride dihydrate (932.3 g; 4131.8 mmol) in portions at 0° C. and the reaction mixture was stirred for 20 h under nitrogen atmosphere while allowing the temperature of the reaction mixture to ambient temperature. The progress of the reaction was monitored by TLC and UPLC. After 20 h the reaction mixture was concentrated under reduced pressure, and the residue obtained was diluted with water (1000 mL). The aqueous mixture was basified with solid sodium bicarbonate (till pH ~9-10) at 5° C. Then chloroform (1500 mL) was added to the aqueous part and stirred for 15 minutes, insoluble inorganic appeared was filtered over a bed of Celite. The bed was washed thoroughly with chloroform (5*500 mL) The organic layer was separated, washed with saturated brine solution (800 mL), dried over anhydrous sodium sulphate, filtered and concentrated to afford methyl 5-amino-6-((3-bromophenyl)amino)nicotinate 5 (350 g, 78.88%) as greyish solid.

$^1$H NMR (400 MHz, DMSO-$d_6$): δ=8.38 (s, 1H, exchangeable proton), 8.13 (s, 1H), 8.06 (s, 1H), 7.70 (d, J=10.00 Hz, 1H), 7.42 (s, 1H), 7.27-7.22 (m, 1H), 7.13-7.10 (m, 1 H), 5.31 (s, 2H, exchangeable proton), 3.80 (s, 3H); LCMS (ESI): m/z: 324.0 (M+H)$^+$.

To a stirred solution of Methyl 5-amino-6-((3-bromophenyl)amino)nicotinate 5 (350 g, 1086.41 mmol) in anhydrous THF (3000 mL) was added Trimethyl orthoformate (172.94 g, 1629.6 mmol) followed by p-Toluenesulphonic acid (pTSA) (61.99 g, 325.92 mmol) in one portion, and the reaction mass was heated to 80° C. under nitrogen atmosphere. The progress of the reaction was monitored by TLC and UPLC. After 3 h, the reaction mixture was allowed to reach ambient temperature, and solvent was removed under reduced pressure. The obtained crude was diluted with water (1000 mL), and aqueous part was basified with sodium bicarbonate till pH ~9-10 while stirring at RT. The stirring was continued for further 1 h. The solid appeared was filtered under suction and dried completely under vacuum to furnish crude mass (380 g, 105.3% mass balance) as and off white solid. The crude was dissolved in chloroform (5000 mL), washed with brine, dried over $Na_2SO_4$, filtered and concentrated under reduced pressure to furnish methyl 3-(3-bromophenyl)-3H-imidazo[4,5-b]pyridine-6-carboxylate 6 (335 g, 92.83%) as off white solid.

$^1$H NMR (400 MHz, DMSO-$d_6$): δ=9.12 (s, 1H), 9.03 (d, J=2.00 Hz, 1H), 8.67 (d, J=2 Hz, 1H), 8.27-8.26 (m, 1H), 8.04-8.01 (m, 1H), 7.73-7.71 (m, 1H), 7.63-7.59 (m, 1H), 3.94 (s, 3H); LCMS (ESI): m/z: 334.0 (M+H)$^+$.

Step 4: Preparation of 2-(3-(3-bromophenyl)-3H-imidazo[4,5-b]pyridin-6-yl)propan-2-ol (7)

Step 5: Preparation of 2-(3-(3-(2,4-dimethoxypyrimidin-5-yl)phenyl)-3H-imidazo[4,5-b]pyridin-6-yl)propan-2-ol (1)

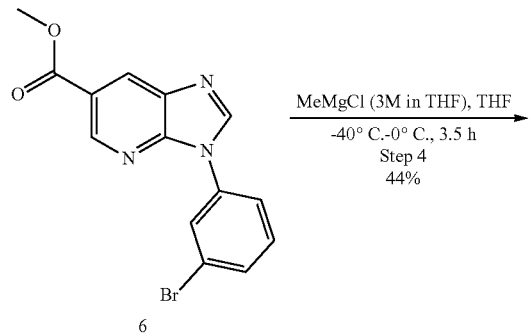

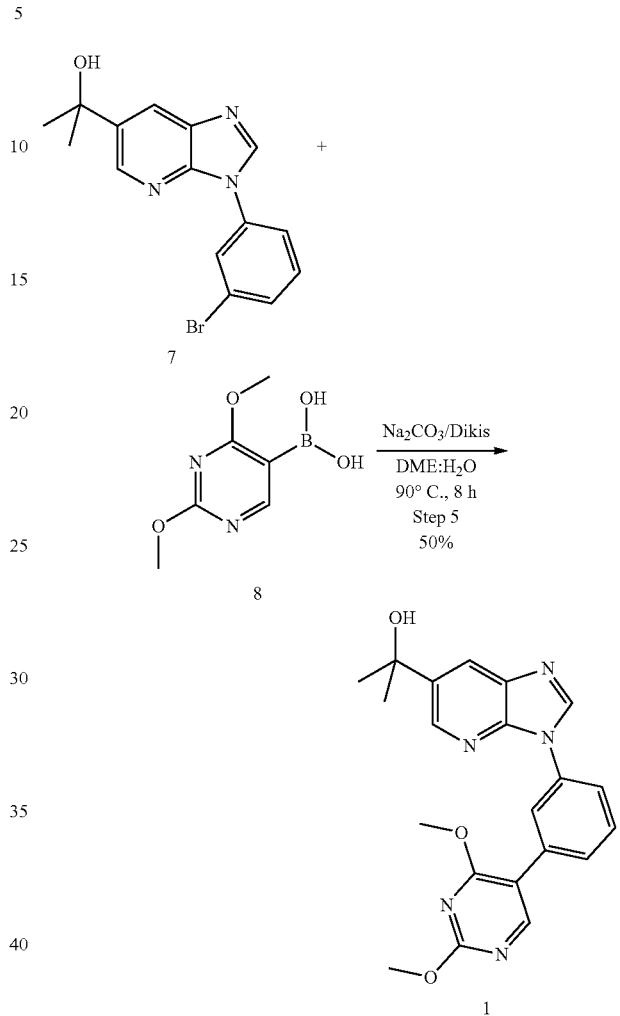

To a stirred Suspension of Methyl 3-(3-bromophenyl)-3H-imidazo[4,5-b]pyridine-6-carboxylate 6 (50 g, 150.53 mmol) in anhydrous THF (600 mL) at −20° C. was added MeMgCl solution [(72 mL, 143.92 mmol); 2M in THF] drop wise of a period of 30 minutes under nitrogen atmosphere. The reaction mixture was stirred for 3.5 h under nitrogen atmosphere while maintained the reaction temperature at −20° C. to 0° C. The progress of the reaction was monitored by TLC and UPLC. After 3.5 h, the reaction mass was quenched with saturated ammonium chloride solution (1500 mL), the aqueous layer was extracted with ethyl acetate (3*1000 mL), combined organic layer was washed with saturated brine solution (500 mL), dried over anhydrous sodium sulphate, filtered and concentrated to furnish crude mass (51 g, 102% mass balance) as brown gum. The crude was purified by flash column over a bed of neutral alumina using 20% ethyl acetate in hexane as eluent to furnish desired product 2-(3-(3-bromophenyl)-3H-imidazo[4,5-b]pyridin-6-yl)propan-2-ol 7 (22 g, 44%) as brown gum.

$^1$H NMR (400 MHz, DMSO-$d_6$): δ=8.95 (s, 1H), 8.62 (s, 1H), 8.33 (s, 1H), 8.23 (s, 1 H), 8.06 (d, J=8.00 Hz, 1H), 7.65 (d, J=8.00 Hz, 1H), 7.59-7.55 (m, 1H), 5.32 (s, 1H, exchangeable proton), 1.55 (s, 6H); LCMS (ESI): m/z: 334.0 (M+H).

To a stirred solution of 2-(3-(3-bromophenyl)-3H-imidazo[4,5-b]pyridin-6-yl)propan-2-ol 7 (0.75 g, 2.25 mmol) in a mixture of 1,2-dimethoxyehane:water [2:1; (45 mL)], was added 2,4-Dimethoxypyrimidine-5-Boronic Acid 8 (0.456 g, 2.48 mmol), followed by $Na_2CO_3$ (0.478 g, 4.51 mmol). The mixture was degased with nitrogen gas for 25 minutes. Bis(triphenylphosphine)Palladium (II) dichloride (0.079 g, 0.112 mmol) was added to the above reaction mixture and was heated to 90° C. under nitrogen atmosphere. The progress of the reaction was monitored by TLC and UPLC. After 15 h, the reaction mixture was allowed to reach ambient temperature and quenched with cold water (75 mL). The aqueous part was extracted with ethyl acetate (3*200 mL), and the combined organic layer was washed with brine (2*50 mL), dried over anhydrous sodium sulphate, filtered and concentrated to furnish crude (0.865 g; mass balance 97.8%) as brown gum. The crude was purified by flash column using 50% ethyl acetate in hexane as eluent to furnish desired product (0.575 g) as off white solid, which was further triturated, filtered and dried under suction to furnish 2-(3-(3-(2,4-dimethoxypyrimidin-5-yl)phenyl)-3H-imidazo[4,5-b]pyridin-6-yl)propan-2-ol (1) (0.5 g, 56.62%) as off white solid.

¹H NMR (400 MHz, DMSO-d$_6$): δ=8.94 (s, 1H), 8.60 (d, J=2.00 Hz, 1H), 8.54 (s, 1H), 8.24 (d, J=2.00 Hz, 1H), 8.13-8.12 (m, 1H), 8.01-7.98 (m, 1H), 7.70-7.63 (m, 2H), 5.3 (s, 1H, exchangeable proton), 3.98 (d, J=4.00 Hz, 6H), 1.55 (s, 6H); LCMS (ESI): m/z: 392.3 (M+H)$^+$, MR: 86.0° C.-93.4° C.

Example 2: In Vitro Inhibition of ³H-Flumazenil Binding

Tissue Preparation

HEK-293 cell lines with stable expression of recombinant GABA $\alpha_3\beta_2\gamma_2$ receptors were cultured (37° C., 5% CO$_2$) in Dulbecco's Modified Eagle Medium (DMEM) with Ultraglutamine 1, 4500 mg/l D-glucose, 10% fetal bovine serum and containing the following antibiotics: zeocin (0.1 mg/ml), hygromycin B (0.15 mg/ml) and G418 (0.5 mg/ml).

When the cultures reached confluency in large culture flasks (175 cm²) the DMEM was removed and the cells were washed once in Dulbecco's Phosphate Buffered Saline (DPBS; KCl: 0.2 g/l, KH$_2$PO$_4$: 0.2 g/l, NaCl: 8 g/l, Na$_2$HPO$_4$: 1.15 g/l). The cells were harvested after addition of 2 ml DPBS to the culture for approximately 5 min followed by gently scraping the cells of the bottom of the culture flask. After addition of another 15 ml DPBS, the cell suspension was transferred to Falcon tubes and centrifuged at 3,000 rpm for 10 min. The pellet was washed once in 15 ml Tris-HCl or Tris-citrate buffer (50 mM, pH 7.1) using an Ultra-Turrax homogenizer and centrifuged at 2° C. for 10 min at 27,000×g. The washed pellet was resuspended in 15 ml Tris-HCl or Tris-citrate buffer (50 mM, pH 7.1) and frozen at −80° C. until the day of the binding experiment.

Assay

On the day of experiment, the membrane preparation was thawed at room temperature and centrifuged at 2° C. for 10 min at 27,000×g. The pellet was resuspended using an Ultra-Turrax homogenizer in Tris-citrate buffer (50 mM, pH 7.1) to 30-150 µg protein per assay and then used for binding assays. Aliquots of 0.5 ml cell suspension were added to 25 µl of test solution and 25 µl of ³H-flumazenil (1 nM, final concentration), mixed and incubated in duplicate for 40 min at 2° C. Non-specific binding was determined using clonazepam (1 µM, final concentration).

All dilutions of test compounds and incubation of assay were performed in glass vials/plates. Solutions of test compounds and ³H-flunitrazepam were prepared 22× the desired final concentration. Compounds were dissolved in 100% DMSO (10 mM stock), diluted in 48% ethanol-water, and tested in triplicate in serial dilutions.

Binding was terminated by rapid filtration onto Whatman GF/C glass fibre filters using a Brandel Cell Harvester, followed by 10 washes with 1 ml ice-cold Tris-citrate buffer. The amount of radioactivity on the filters was determined by conventional liquid scintillation counting using a using a Tri-Carb™ counter (PerkinElmer Life and Analytical Sciences). Specific binding is total binding minus non-specific binding.

Results

TABLE 1

$K_i$ and IC$_{50}$ values for compound 1.

| Compound | $K_i$ (µM) | IC$_{50}$ (µM) |
|---|---|---|
| 2-(3-(3-(2,4-dimethoxypyrimidin-5-yl)phenyl)-3H-imidazo[4,5-b]pyridin-6-yl)propan-2-ol (1) | 0.015 | 0.038 |

The IC$_{50}$ value is the concentration of the test substance which inhibits the specific binding of ³H-flumazenil by 50%, $$IC_{50} = \text{(applied concentration of 1)} * \frac{1}{\left(\frac{C_0}{C_X} - 1\right)}$$

where $C_0$ is the specific binding in the control assay, and $C_X$ is the specific binding in the test assay.

Conclusion 2-(3-(3-(2,4-dimethoxypyrimidin-5-yl)phenyl)-3H-imidazo[4,5-b]pyridin-6-yl)propan-2-ol (1) was found to have a $K_i$ value of 0.015 µM and a IC$_{50}$ value of 0.038 µM.

Example 3: Oocyte Electrophysiology

The assay reported here is performed to determine the in vitro functional potency as well as efficacy of PAMs at the major brain GABA$_A$ receptors subtypes. To establish this, a full concentration response profile was determined at a GABA concentration giving rise to 5-20% of the maximal GABA-evoked response from $\alpha1\beta2\gamma2$, $\alpha2\beta2\gamma2$, $\alpha3\beta2\gamma2$ and $\alpha5\beta2\gamma2$ receptors expressed in Xenopus laevis oocytes.

Xenopus laevis Oocyte Preparation

Collagenase defolliculated X. laevis oocytes were obtained from Ecocyte Bioscience. For injection, the oocytes were placed in a custom designed chamber in Mod. Barth's solution (90 mM NaCl, 1 mM KCl, 0.66 mM NaNO$_3$, 2.4 mM NaHCO$_3$, 0.74 mM CaCl$_2$, 0.82 mM MgCl$_2$, 100 µg/ml Gentamicin and 10 mM HEPES adjusted to pH 7.55) and injected with 25-50 nl of cRNA mixture using a Pico Pump (WPI). The cRNA mixture contain GABA$_A$R subunits $\alpha_x$, $\beta_2$, and $\gamma_{2s}$ in the ratio of 3:1:3 and in a total concentration of 0.5 µg/µl. Following injection, oocytes were maintained at 18° C. in Mod. Barth's for 1-5 days.

Two-electrode Voltage Clamp Experiments

Electrophysiological responses from X. laevis oocytes were measured using the two-electrode voltage clamp technique. Single oocytes were placed in custom designed recording chambers that were continuously perfused with ≥2 ml/min OR2 (90 mM NaCl, 2.5 mM KCl, 2.5 mM CaCl$_2$, 1 mM MgCl$_2$ and 5 mM HEPES pH 7.4). The experimental assay solution was a standard OR2 buffer solution which had a measured osmolarity of approximately 180mOsm. Recording electrodes were fabricated from borosilicate glass tubings with filament (Sutter BF150-110-10) using a DMZ-Universal puller (Zeitz Instrument), backfilled with 2 M KCl and when submerged into OR2 solution the electrode resistances were in the range of 0.5-1 MΩ. The oocyte was impaled using manual micro manipulators and allowed to equilibrate at a holding potential of −50 mV to −80 mV for at least 1 min to ensure a maximal leak current of 100 nA before the experiment was initiated. The holding potential was normally set at −60 mV, which is significantly lower than a typical resting potential of −25 mV. In case current amplitudes were low in a batch of oocytes, a holding potential of −80 mV was used provided that the leak current did not exceed 100 nA. Currents were amplified by a Geneclamp 500B amplifier (Axon), low-pass filtered at 20 Hz, digitized at 200 Hz by a Digidata 1322A (Axon) and then recorded as well as analyzed by a PC (Compaq Evo) using the pClamp9 suite (Axon).

Compound solutions were applied through a capillary tube, with an inner diameter of 1.5 mm (Modulohm 214813), placed approximately 2 mm from the oocyte and connected through Teflon tubing to a Gilson 233XL autosampler. Gilson 735 software suite was used to control all the Gilson equipment (233XL autosampler, 402 diluter and Minipuls 3 pumps) and to trigger recording by pCLAMP9. A flow rate of 2.5 ml/min through the capillary tube during applications ensured a rapid exchange of liquid surrounding the oocyte. The application length was set to last 60 s which was sufficient to obtain peak currents. The time interval between recordings was 5 min, during which the oocyte was perfused with OR2 through the capillary tube as well.

Experimental Data

For each experimental data set, GABA was dissolved in OR2 in a concentration known to give rise to $EC_5$-$EC_{20}$ elicited currents for a given $GABA_A$ receptor subtype combination (0.5-5 µM) and this solution was then used for controls as well as a stock solution for dissolving the compounds to test in the experiment. A complete experimental set contained four control traces of GABA, a reference 0.5 µM diazepam trace, 10 GABA control traces, and finally traces of a test compound in increasing concentrations. The individual oocytes were discarded after one experimental set.

Modulatory effects of diazepam were calculated by comparing the diazepam trace to the control trace immediately before. Likewise, modulatory effects of the compound in the test traces were obtained by comparing to the control immediately before the test traces. To enable comparison of effects of a compound between individual oocytes, all compound potentiations were normalized to the control diazepam potentiation on the same oocyte.

Results

The assay was conducted for compounds 1 and 9, see below, and the results are presented in FIG. 1.

Conclusion

As can be seen form the concentration response profiles, the modulation by compounds 1 and 9 varies, especially regarding the modulation of $\alpha_1\beta_2\gamma_2$ receptor. Importantly, the modulation of the $\alpha_1\beta_2\gamma_2$ receptor is close to zero for compound 1, whereas it is clearly negative for compound 9. This Example also demonstrates that a relatively small structural difference between two molecules have large impact on the biological activity.

Example 4: Acute- and Chronic Effects of Compound 1 on Mechanical Allodynia in Chronic Constriction Injury (CCI) in Rats Method Animals:

Male SPRD rats (Taconic), 140-160 grams at surgery

Surgery:

Anesthesia was induced and maintained by 2.5% isoflurane combined with oxygen (30%) and nitrous oxide (68%). The sciatic nerve was exposed at the mid-thigh level proximal to the sciatic trifurcation. Four chromic gut ligatures (4/0) (Ethicon, New Brunswick, N.J.) were tied loosely around the nerve, 1-2 mm apart, such that the vascular supply was not overtly compromised. The overlying muscle was closed in layers with 4/0 synthetic absorbable surgical suture. The skin was closed with 1-2 clips.

Behavioural Testing of Nerve-injured Rats:

3-14 days after surgery, the animals were monitored for the presence of mechanical allodynia. Prior to assessment, individual rats were removed from their home cage and allowed to habituate for 60 min in an openly ventilated 15×20 cm white Plexiglass testing cage, placed upon an elevated metal grid allowing access to the plantar surface of the injured hindpaw. The presence of mechanical allodynia was assessed using a series of calibrated von Frey hairs (lower limit=0.1 and upper limit=26 g, Stoelting Co, Wood Dale Ill.), which were applied to the plantar surface of the paw with increasing force until an individual filament used just started to bend. The filament was applied for a period of 1-2 s and was repeated 5 times at 1-2 s intervals. The filament that induced a paw withdrawal in 3 out of 5 applications was considered to represent the paw threshold threshold (PWT) for a mechanical allodynic response to occur. Only those animals showing distinct neuropathic pain behaviours (allodynia) were included in drug testing experiments. Animals showing PWT less than/or equal to 4 g on the ipsilateral paw and PWT more than/or equal to 8 g on the contralateral paw were considered to be allodynic. On drug testing days the experimenter was blinded to the treatment. Drug treatment took place day 15 post surgery.

Drug Treatment:

Acute Drug Effect:

Compound 1: 1, 3, 10 mg/kg, 10 ml/kg, per oral administration.

Pretreatment: 2 hrs

Morphine-hydrochloride: 6 mg/kg free base weight, 1 ml/kg, subcutaneous administration. Pretreatment: 30 minutes Vehicle for Compound 1 and morphine: 5% DMSO+30% (2-Hydroxypropyl)-β-cyclodextrin (HPBCD) in water.

Statistical evaluation: one way ANOVA followed by Fishers LSD test for multiple comparisons.

Chronic Drug Effect:

Compound 1: 1, 3, 10 mg/kg, 10 ml/kg, per oral administration once daily for 7 days.

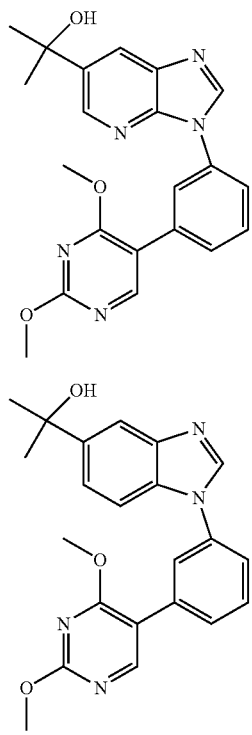

Morphine hydrochloride: 6 mg/kg free base weight, 1 ml/kg, subcutaneous administration once daily for 7 days. On day 8, mechanical allodynia was monitored by applying von Frey filaments ("basal level") where after the rats were administered Compound 1 or morphine hydrochloride, and mechanical allodynia was monitored by von Frey filaments again 2 hrs and 3 hrs after dosing (Compound 1) or 30 minutes after dosing (morphine hydrochloride).

Vehicle: 5% DMSO+30% HPBCD (in water)

Statistical evaluation: one way ANOVA followed by Fishers LSD test for multiple comparisons.

Results

Figure 2:
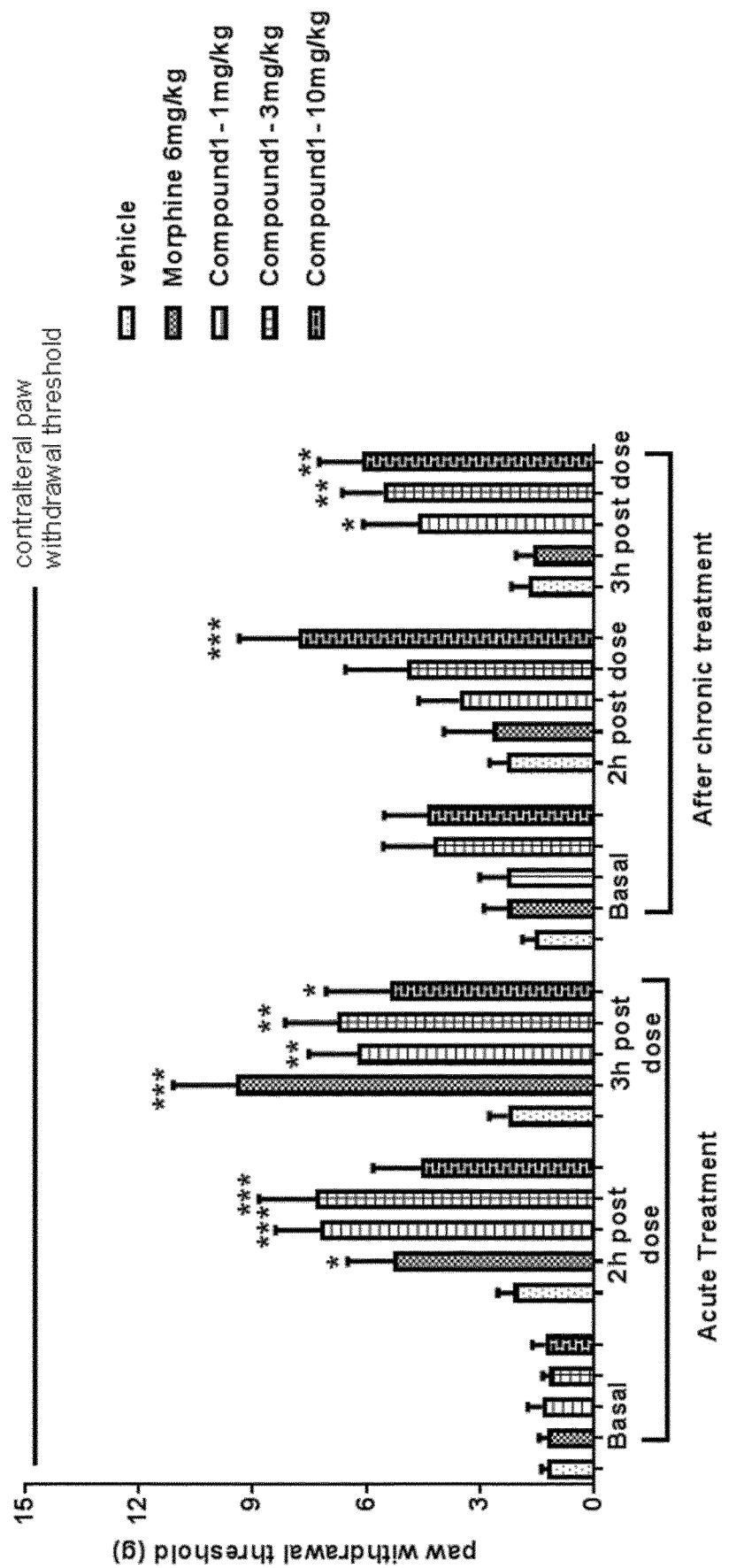
FIG. 2. Effects of compound 1 after acute dosing on scratching behaviour in male CD-1 mice. Acute treatment with compound 1 reversed the mechanical allodynia in rats subjected to CCI lesions with a minimal effective dose less than or equal to 1 mg/kg after oral administration. After 7 days of chronic treatment, a significant analgesic effect of all 3 doses were maintained, while the effect of morphine (6 mg/kg) was completely lost. Morphine was administered subcutaneously. Chronic constriction injury (CCI) in male Sprague Dawley's rats was performed as described by Bennette and Xie's, (1998). The animals were tested after 14 days of surgery. $p<0.01$,**$p<0.0001$ vs vehicle, Two-way ANOVA Fisher's LSD posttest, n=7-9.

Acute dosing of Compound 1 resulted in significant amelioration of neuropathic pain behaviours as assessed by monitoring mechanical allodynia using von Frey hairs. Lowest tested dose of 1 mg/kg, and 3 mg/kg significantly enhanced paw withdrawal threshold as compared to vehicle treatment, monitored 2 hrs and 3 hrs post treatment, see FIG. 2 (2 hrs: $p<0.01$, 3 hrs: $p<0.05$, One way ANOVA Followed by Fishers LSD post hoc testing). 10 mg/kg just failed to reach statistical significance. Morphine hydrochloride 6 mg/kg also significantly enhanced paw withdrawal threshold as compared to vehicle treatment 2 hrs and 3 hrs post treatment ($p<0.05$ and $p<0.001$ vs. vehicle respectively). After 7 days of daily dosing of Compound 1, significant enhancement of the paw withdrawal threshold was maintained after 1-3, and 10 mg/kg pretreated 3 hrs prior to testing ($p<0.05$, 0.01 and 0.01 vs. vehicle respectively) and 10 mg/kg dosed 2 hrs prior to testing ($p<0.001$ vs. vehicle) (one way ANOVA followed by Fishers LSD post hoc testing). In contrast, chronic treatment with morphine prior to acute drug administration completely abolished the allodynic effect indicating tolerance development (FIG. 2).

Conclusion

This Example demonstrates that compound 1 ameliorates neuropathic pain behaviours after acute drug administration and that the effect is maintained after chronic drug administration, indicating lack of tolerance development. In contrast, the effect of an opioid, morphine hydrochloride, is completely lost after chronic drug administration due to development of tolerance.

Example 5: Acute Effects of Compound 1 on Compound 48/80 Induced Scratching in Male CD-1 Mice Method Animals:

Male CD-1 mice (22-30 g) (InterVivo Solutions, Canada)

Drug Treatment:

Animals were dosed with one of the following treatments: compound 1, vehicle (negative control) or diphenhydramine hydrochloride (positive control); N=8 mice per group. Compound 1 was dosed by oral gavage at a concentration of 3, 10 and 30 mg/kg in vehicle (5% DMSO+30% HPBCD in water) 30 minutes prior to testing. Diphenhydramine hydrochloride was dosed by oral gavage at a dose of 60 mg/kg in 5% Tween 80 in distilled water (BEW=1.14) 60 minutes prior to testing. All treatments were dosed at a dosing volume of 10 ml/kg. Compound 48/80 was administered intradermal in the neck at 50 ug/0.02 ml in saline.

Behavioral Monitoring:

Visual observation of bouts of scratching over 30 minutes. Visual assessments were performed blinded to treatment.

Statistical Evaluation:

One way ANOVA followed by Fishers LSD test for post hoc comparisons.

Results

Figure 3:
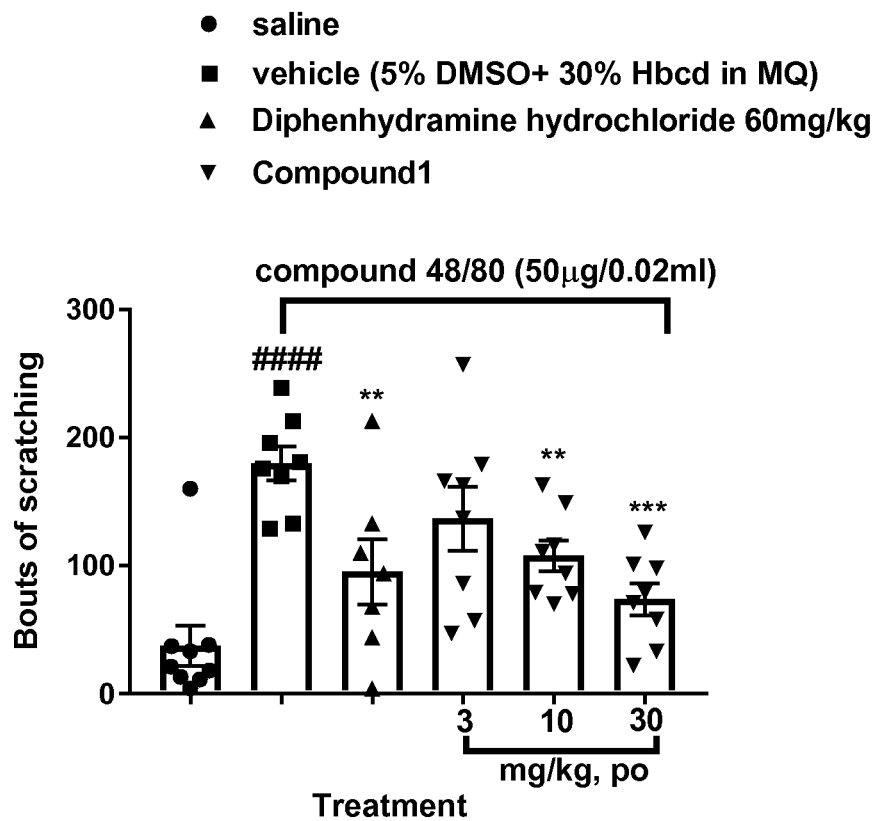
FIG. 3. Effects of compound 1 after acute- and chronic dosing on paw withdrawal threshold in CCI lesioned rats. Compound 1 dose dependently reduced compound 48/80 induced scratching behavior in CD-1 male mice. Compound 48/80, injected in 50 µL subcutaneously at the nape of neck, induced a marked and significant increase in bouts of scratching as compared to vehicle injected mice. The histaminergic H1 antagonist, Dipenhydramine hydrochloride was used as reference and administered orally 60 min before Compound 48/80 while compound 1 was administered orally 30 min prior to compound 48/80 administration. ####$p<0.0001$ vs. Saline; *$p<0.001$, $p<0.01$, vs vehicle+compound 48/80, One-way ANOVA Fisher's LSD post hoc test, n=7-9.

Compound 1 significantly relieved itching, as assessed as bouts of scratching, with a minimal effective dose of 10 mg/kg as compared to vehicle treatment ($p<0.01/0.001$ vs. vehicle treatment for 10- and 30 mg/kg respectively, One way ANOVA followed by Fishers LSD test for post hoc comparisons), see FIG. 3.

Conclusion

This Example demonstrates that compound 1 significantly ameliorate scratching behaviour in mice indicating positive effects on itching.

Example 6: Acute Effects of Compound 1 on Exploratory Locomotor Activity in Male Sprague Dawley (SD) Rats Method Animals:

Male SD rats (180-250 grams, NTac:SD, Taconic, Denmark)

Drug Treatment:

Animals were dosed with one of the following treatments: Vehicle (5% DMSO+30% HPBCD in water) or compound 1 (3, 10, 30 mg/kg, 10 ml/kg, per oral administration), 120 minutes prior to testing. n=6-7 pr dose group.

Behavioral Monitoring:

2 hrs post dosing, the rats were placed individually into novel standard home cages with reduced sawdust bedding. The cages were placed in frames equipped with photocells and beams allowing for automatic recording of locomotor behaviour (TSE MoTil, Germany). The exploratory locomotor activity was recorded for 30 minutes.

Statistical Evaluation:

One way ANOVA followed by Fishers LSD test for post hoc comparisons.

Results

Figure 4:
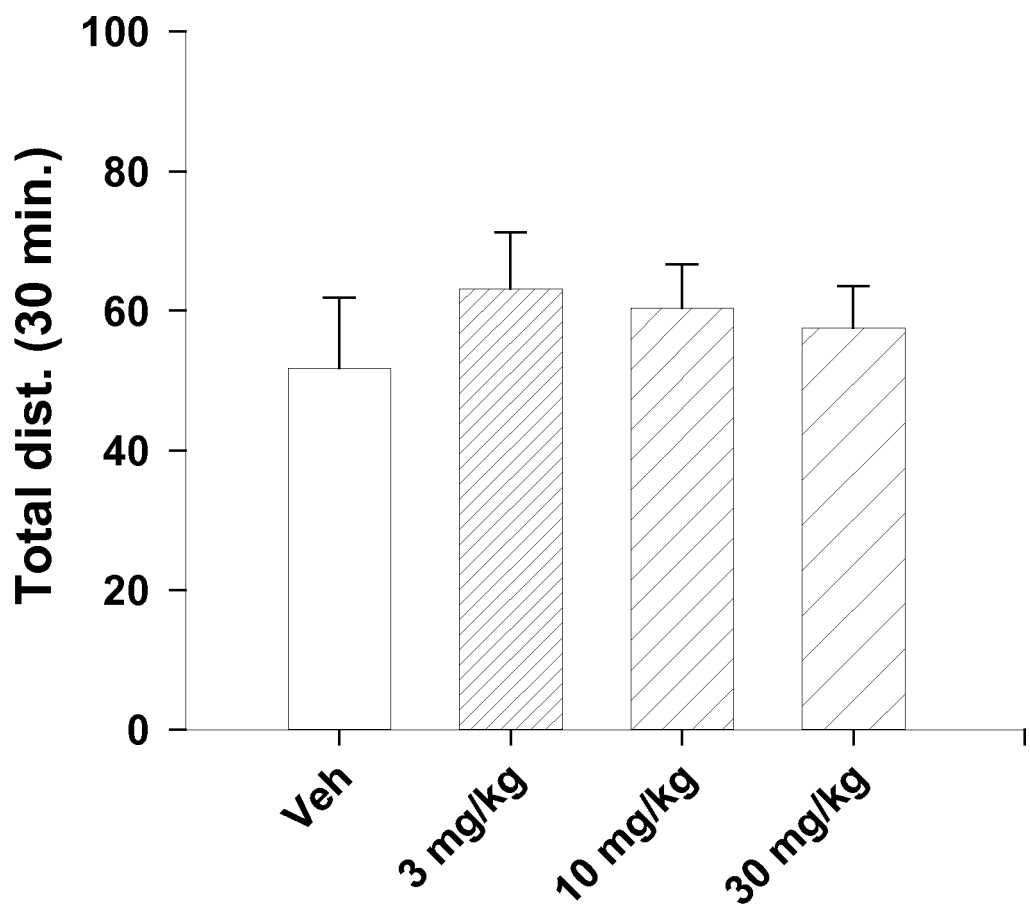
FIG. 4. Effects of compound 1 on exploratory locomtor activity in male SD rats. Compound 1 dosed up to 30 mg/kg, corresponding to a free brain concentration of 494 did not affect exploratory locomotor activity in male Sprague Dawley rats (p >0.05 two way repeated measures ANOVA with time and dose as factors). Compound 1 was administered orally at 3, 10 and 30 mg/kg, 10 ml/kg, 120 minutes prior to introducing the rats into novel homecages under dim light conditions. The activity of the rats was automatically registered for 30 minutes (TSE MoTil, Germany).

Compound 1 did not exert any effect on exploratory locomotor activity in male SD rats in the highest dose tested (30 mg/kg) (One way ANOVA followed by Fishers LSD test for post hoc comparisons), see FIG. 4.

Conclusion

This Example demonstrates that compound 1 did not affect exploratory locomotor activity in rats in the doses tested, indicating lack of propensity to cause sedation.

Example 7: Acute Effects of Compound 1 on Rotarod Performance in Male Sprague Dawley (SD) Rats Method Animals:

Male SD rats (150-180 grams, NTac:SD, Taconic, Denmark)

Drug Treatment:

Animals were dosed with one of the following treatments: Vehicle (5% DMSO+30% HPBCD in water), compound 1 (3, 10, 30 mg/kg, 10 ml/kg, per oral administration) or Diazepam 10 mg/kg (10 ml/kg, per oral administration) 120 minutes- or 60 minutes prior to testing respectively. n=6-7 pr dose group.

Behavioral Monitoring:

The rats were trained on an accelerating rotarod (4-40 rpm, PanLab), one trial of 5 minutes per day, for two days prior to drug testing. Only rats that were able to stay on the rotating rod for more than 90 seconds after two days of training were included in the study. At the day of testing, the rats were placed on the rotating rod, accelerating with a speed of 4-40 rpm/5 minutes with the minimum time possible to spend on the rod designated as 0 s, and the maximum time spent on the rod set at 300 s. Compound 1 was dosed 2 hrs prior to testing, while the positive control, Diazepam, was dosed 60 minutes prior to testing.

Statistical Evaluation:

One way ANOVA followed by Fishers LSD test for post hoc comparisons.

Results

Figure 5:
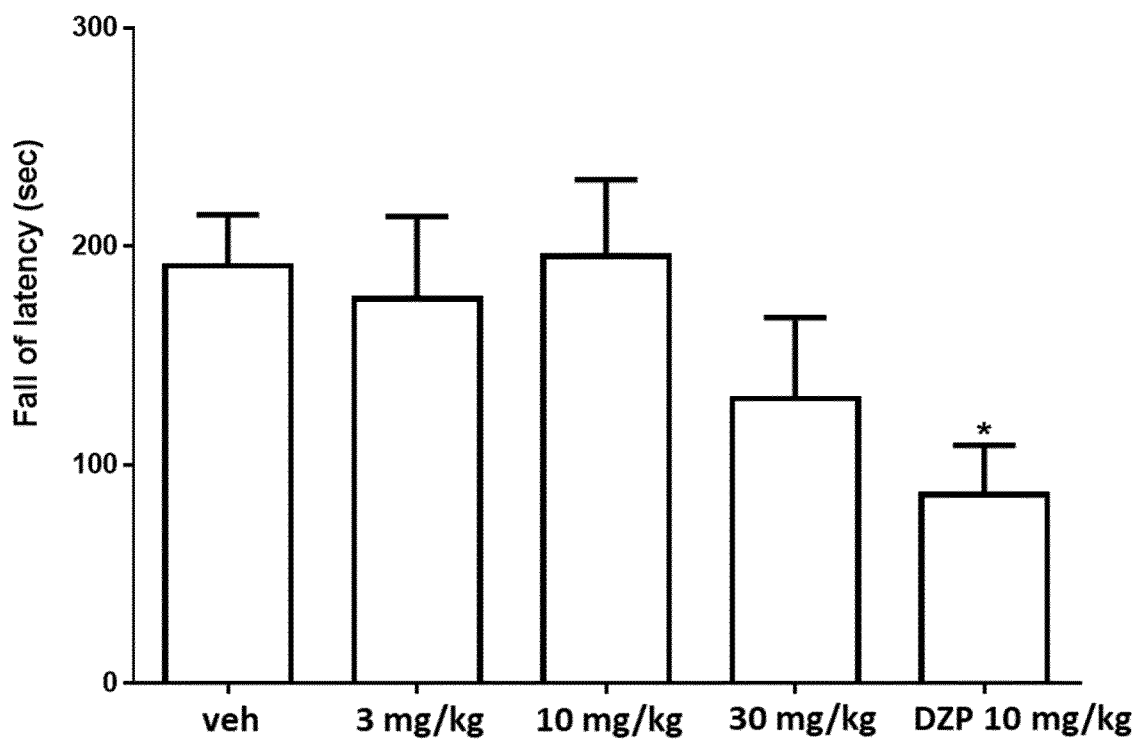
FIG. 5. Effects of compound 1 on rotarod performance in male SD rats. Compound 1 dosed up to 30 mg/kg did not impair rats ability to maintain balance on an accelerating rotating rod, measured as latency to fall of the rod. In contrast, the non-selective $GABA_A$ receptor positive modulator, Diazepam, significantly shortened the latency to fall off (p<0.05). Compound 1 and diazepam were administered orally 2 h and 1 h before teststart respectively. Rats were trained on the rota rod for two days at 4-40 rpm for 5 min before evaluating the drug effects on the $3^{rd}$ day. Rats which failed to run for more than 90 sec after training were not included in the experiment. *$p<0.05$, vs vehicle, One-way ANOVA Fisher's LSD posttest, n=6-7.

Compound 1 did not affect the rat's ability to balance on the accelerating rod, measured as latency to fall, in the highest dose tested (30 mg/kg) compared to vehicle treated rats. In contrast, Diazepam significantly shortened the time to fall off the rod (p<0.05 vs. vehicle treatment) (One way ANOVA followed by Fishers LSD test for post hoc comparisons), see FIG. 5.

Conclusion

This Example demonstrates that compound 1 did not impair the rat's ability to maintain balance on an accelerating rod in the doses tested, indicating lack of propensity to cause motor impairments.

Example 8: Plasma Protein Binding Estimated by Rapid Equilibrium Dialysis

The purpose of this assay is to determine the degree of binding of a test compound to plasma proteins.

Method

Rapid Equilibrium Dialysis (RED) Devices:

Disposable inserts comprised of two side-by-side chambers (plasma and buffer) separated by a vertical cylinder of dialysis membrane (MWCO ca. 8000) were used. The RED devices were placed in a Teflon Base Plate and incubated for 4 hours at 37° C. on a Heidolph incubator set to 100 rpm.

Assay

The assay was performed in liquid handling system according to the following assay description:

Preparation of spiked plasma

Place relevant number of RED devices in Teflon Base plate and pre-heat the plate on the incubator.

Add 400 µl plasma to plasma chamber and 600 µl PBS-buffer to buffer chamber.

Incubate for 4 hours at 37° C. on the Heidolph incubator set to 140 rpm.

After incubation, transfer 50 µl from the plasma chambers to eppendorf tubes and add 50 µl PBS-buffer.

Correspondingly, transfer 50 µl from the buffer chambers to eppendorf tubes and add 50 µl plasma.

Precipitate all samples with 300 µl MeCN.

Centrifuge for 25 minutes at 5° C. and 14000 rpm (16000 g).

Transfer supernatant to HPLC vials with and equal volume of MilliQ water

Analyse by LC-MS/MS with SRM detection

Results

The protein binding was calculated using the following formula:

$$\% \text{ Protein Binding} = \left(1 - \frac{A_{buffer}}{A_{plasma}}\right) * 100\%$$

Free fraction: fu=100−% Protein Binding where, $A_{buffer}$ is the Area determined by LC-MS/MS for the sample from the buffer chamber.

$A_{plasma}$ is the Area determined by LC-MS/MS for the sample from the plasma chamber.

The plasma free fraction of compound 1 was 16% in mouse and 19% in rat.

Conclusion

Compound 1 is abundantly free in the plasma to exert pharmacological effects.

Example 9: Brain Tissue Binding

The purpose of this example is to evaluate protein binding of compound 1 to rat brain homogenate using Rapid Equilibrium Dialysis (RED) method.

Material and Equipment

Rat Brain Homogenate

Rat brain protein fraction was prepared from fresh brain tissues isolated from adult Wistar rats. Male Wistar rats (Harlan, Netherland) are euthanized (according to approved method) and brain tissue was collected immediately. The white matter was dissected out, and a tissue homogenate (10% w/v) is prepared in phosphate buffered saline, pH 7.4. This fraction called the brain homogenate and was used in the experiment.

Procedure for Equilibrium Dialysis

Preparation of Teflon Base Plate

Teflon® Base Plate wells were rinsed with 20% ethanol for 10 minutes. The ethanol was removed and the wells were rinsed twice with distilled water, thereafter the plate was allowed to dry before use.

Equilibrium Dialysis

1 µl compound 1 (2 mM stock in 100% DMSO) was added into 200 µl brain extract (final concentration 10 µM). 200 µl of sample was placed into the sample chamber. 350 µl of 10 mM PBS was added into the buffer chamber. The unit was covered with sealing tape and incubate at 37° C. on an orbital shaker at approximately 350 rpm for 4 hours to achieve equilibrium. Equal volumes from both the buffer and the extract chambers were then removed and placed in separate micro centrifuge tubes.

Procedure for Sample Analysis

50 µl of each post-dialysis sample was pipetted from the buffer and the extract chambers into separate micro centrifuge tubes. 50 µl of extract was added to the buffer samples, as well as an equal volume of PBS to the collected extract samples. 300 µl of precipitation buffer (90/10 acetonitrile:water containing 0.1% formic acid+internal standard viz. Tolbutamide or Ibuprofen, 5 µg/ml)) was added to precipitate protein and release compound, which were vortexed and incubated 30 minutes on ice before 10 minutes centrifuge at 13,000-15,000 g. The supernatant was then transferred to a vials or 96-well plate, and quantitative measurements by LC/MS/MS were performed. The concentration of compound 1 in the buffer and extract chambers were determined from peak areas relative to the internal standard.

Results

The fraction unbound (fu) was calculated using the following formula:

$$f_{u,diluted} = \frac{A_{buffer}}{A_{brain\ homogenate}}$$

-continued $$f_{u,undiluted} = \frac{\frac{1}{D}}{\frac{1}{f_{u,diluted}} + \frac{1}{D}} * 100\%$$

where, $A_{buffer}$ is the Area determined by LC-MS/MS for the sample from the buffer chamber.

$A_{brain\ homogenate}$ is the Area determined by LC-MS/MS for the sample from the brain homogenate chamber.

Reference compounds: Haloperidol (high binding) and Caffeine (low binding).

The free fraction of compound 1 in the brain tissue was 7% in rats.

Conclusion

Compound 1 is abundantly free in the brain to exert pharmacological effects.

Example 10: Pharmacokinetic Profile

The purpose of this example is to obtain pharmacokinetic data. Plasma samples were typical taken at 6-8 time points (N=3-4). Samples were analysed using a long standard curve using 10 standards. The plasma samples were protein precipitated and diluted using a liquid handling system following analysis using LC-MS/MS.

Assay

Preparation of Standards

Two individual sets of standards were typical prepared in the following concentration levels: 1, 3, 10, 100, 300, 1,000, 3,000, 5,000 and 10,000 ng/ml. The first set of standards was analysed in the beginning of the run and was used for calibration. The second set of standards was analysed in the end of the run, and was used as QC's.

Plasma Sample Preparation

50 µl plasma was precipitated with 150 µl internal standard in acetonitrile

Following centrifugation 25 min at 5° C. at 16,000 g (Eppendorf tubes) or 3,000 g microtiter plate (MTP)

50 µl supernatant and 150 Milli-Q water were transferred to HPLC vial/MTP

Results

Acceptance Criteria

Each point on the calibration curves is allowed to vary 15% from the nominal value (LLOQ can vary 20%). A point can be excluded if it varies more. The standard curve should as minimum contain of 5 points and two consecutive points may not be excluded. The QC's has the same acceptance criteria as the standards in the calibration curve.

Pharmacokinetic parameters were calculated in WinNonlin.

TABLE 2

Pharmacokinetic parameters. Compound 1 was dosed in a clear solution of 30% HP-Beta-CD and 5% DMSO.

| Route | Dose (mg/kg) | $AUC_{(0-8\ h)}$ (h*ng/ml) | $C_0$ (ng/ml) | $t_{1/2}$ (h) | Cl (l/h/kg) | $V_z$ (l/kg) | B/P |
|---|---|---|---|---|---|---|---|
| IV | 0.5 | 985 | 863 | 4.3 | 0.38 | 2.4 | 0.5 |

TABLE 3

Pharmacokinetic parameters. Compound 1 was dosed in a clear solution of 30% HP-Beta-CD and 5% DMSO.

| Dose (mg/kg) | $AUC_{(0-24\ h)}$ (h*ng/ml) | $C_{max}$ (ng/ml) | $T_{max}$ (h) | B/P 3 h |
|---|---|---|---|---|
| 1 | 1134* | 163 | 4 | 0.4 |
| 3 | 8005 | 552 | 6 | 0.5 |
| 10 | 34528 | 2267 | 8 | 0.5 |
| 30 | 98537 | 6591 | 4 | 0.6 |

*AUC calculated 0-8 h, concentration after 8 h was 149 ng/ml.

Conclusion

Compound 1 shows long half-life and low clearance in rat. Compound 1 also shows dose linearity ($C_{max}$), high plasma exposure and high exposure.

Example 11: Intrinsic Clearance Study Using Human and Rat Hepatocytes

In this assay, compound 1 was incubated with cryopreserved hepatocytes for different time points and disappearance of compound 1 was monitored by LC-MS/MS. Conditions used in the assay are summarized below.

Compound concentration in assay: 1 µM

Time of incubations with hetaocytes: 0, 15, 30, 60, 90 and 120 minutes at 37° C. with 5% $CO_2$ Hepatocyte cell density: 106 cells/ml Assay volume: 500 µl No. of replicates: 2

Reference compound: Testosterone (High clearance)

Results

TABLE 4

Hepatocyte clearance in human and rat.

| Species | Hepatocyte clearance $Cl_{int\ in\ vivo}$ (µl/min/million cell) |
|---|---|
| Human | 1.87 |
| Rat | 2.11 |

Conclusion

Compound 1 has low clearance in human and rat hepatocytes.

The invention claimed is:
1. A compound of formula 1:

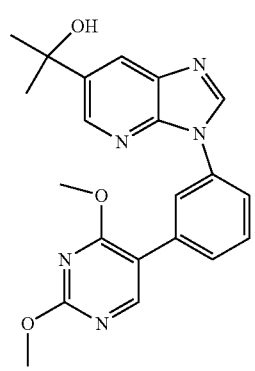

or a pharmaceutically acceptable salt thereof.

2. A pharmaceutical composition comprising a therapeutically effective amount the compound defined in claim 1, or a pharmaceutically acceptable salt thereof.

3. A method for treating neuropathic pain and/or itch in a subject in need thereof comprising administering to the subject a compound of claim 1, or a pharmaceutically acceptable salt thereof.

4. The method of claim 3, wherein the subject is in need of treatment of neuropathic pain.

5. The method of claim 4, wherein the neuropathic pain is allodynia.

6. The method of claim 3, wherein the subject is in need of treatment of itch.

7. The method of claim 6, wherein the itch is Pruritus.

8. The method of claim 6, wherein the itch is caused by a skin condition.

9. The method of claim 8, wherein the skin condition is psoriasis.

10. The method of claim 8, wherein the skin condition is eczema.

11. The method of claim 3, wherein the subject is in need of treatment of neuropathic pain and itch.

* * * * *